(12) United States Patent
Maglione et al.

(10) Patent No.: US 8,257,411 B2
(45) Date of Patent: Sep. 4, 2012

(54) METHOD FOR TREATMENT OF VARICES

(75) Inventors: Franco Maglione, Naples (IT); Tiziano Caldera, Cambs (GB); Fabio Coluccia, Milan (IT)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 863 days.

(21) Appl. No.: 11/637,377

(22) Filed: Dec. 12, 2006

(65) Prior Publication Data

US 2007/0100329 A1 May 3, 2007

Related U.S. Application Data

(63) Continuation-in-part of application No. 10/675,461, filed on Sep. 30, 2003, now abandoned.

(51) Int. Cl.
*A61B 18/18* (2006.01)
(52) U.S. Cl. .................. 607/89; 607/88; 606/9; 606/15
(58) Field of Classification Search .................. 128/898; 606/15, 27, 9; 607/88–94
See application file for complete search history.

(56) References Cited

U.S. PATENT DOCUMENTS

| | | | | |
|---|---|---|---|---|
| 5,188,602 A * | 2/1993 | Nichols | ......................... | 604/113 |
| 6,106,514 A * | 8/2000 | O'Donnell, Jr. | .................. | 606/9 |
| 6,176,854 B1 * | 1/2001 | Cone | ............................... | 606/15 |
| 6,200,332 B1 * | 3/2001 | Del Giglio | ....................... | 607/89 |
| 6,660,000 B2 * | 12/2003 | Neuberger et al. | ................ | 606/9 |
| 2002/0026225 A1 * | 2/2002 | Segal | ............................... | 607/89 |
| 2004/0092913 A1 * | 5/2004 | Hennings et al. | .................. | 606/3 |
| 2005/0015123 A1 * | 1/2005 | Paithankar | ....................... | 607/88 |
| 2006/0069417 A1 * | 3/2006 | Farley et al. | ................... | 607/101 |
| 2006/0189967 A1 * | 8/2006 | Masotti et al. | ................... | 606/15 |
| 2006/0189979 A1 * | 8/2006 | Esch et al. | ....................... | 606/49 |
| 2008/0249519 A1 * | 10/2008 | Goldman et al. | ............... | 606/27 |
| 2010/0063493 A1 * | 3/2010 | Anastasie | ....................... | 606/15 |

* cited by examiner

*Primary Examiner* — Ahmed Farah
*Assistant Examiner* — Jeffrey Lipitz
(74) *Attorney, Agent, or Firm* — BJ Associates; Bolesh J. Skutnik

(57) ABSTRACT

A minimally invasive method for treating varices including pelvic varices in females, varicoceles, and also oesophageal varices is disclosed. The method comprises the steps of inserting a catheter device into the blood vessels of a patient and advancing the distal end of the catheter to reach the varix or varices. The insertion may be made in the femoral vein or in other vessels as appropriate. Preferably, x-ray, angiography, or other imaging techniques are used to visualize and position the catheter. An optical fiber or optical fiber bundle is then inserted into the catheter and the distal end is advanced to a predetermined point near the varix or varices. Laser energy of preferably 980 nm is then transmitted to the varix to close the blood vessel. Imaging techniques such as angiographies may again be performed to confirm closure of the vein. The method is an out-patient procedure that requires no incision or general anesthesia, requires no recovery time, and does not require that any foreign objects be left in the body. This method has been shown to have a higher success rate than previous embolization and surgical procedures.

9 Claims, 1 Drawing Sheet

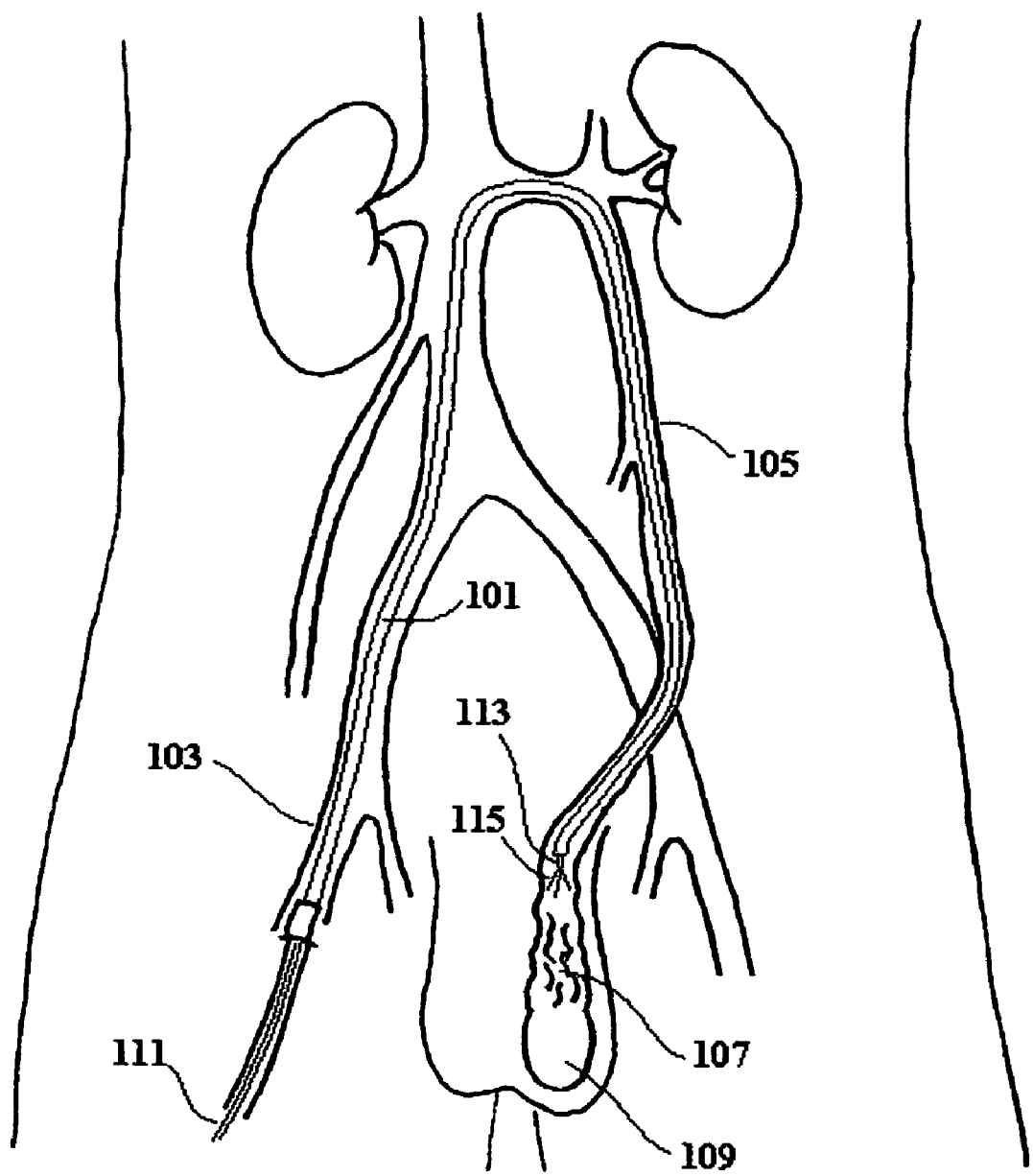

METHOD FOR TREATMENT OF VARICES

BACKGROUND OF THE INVENTION

1. Reference to a Related Case

This application is a continuation-in-part of U.S. patent application Ser. No. 10/675,461 filed on Sep. 30, 2003 now abandoned by Franco Maglione, Tiziano Caldera, Fabio Coluccia, inventors, entitled "METHOD FOR TREATMENT OF VARICES", and incorporated by reference herein.

2. Field of the invention

The invention relates to the field of treatment for male and female reproductive varices, in particular for varicoceles in men and pelvic varices in women, and includes oesophageal varices.

3. Information Disclosure Statement

Varices are uneven, permanent dilations of veins than can occur in numerous areas of the body, and are very common in the superficial veins of the lower limbs (varicose, spider veins). One manifestation of these varices that occurs in men, and is the most common cause of male infertility, is the varicocele. Between 10 and 20% of post-pubescent males are affected by varicoceles, and 20-40% of all infertile males have varicoceles. A varicocele specifically refers to dilatation and tortuosity of the pampiniform plexus. Pampiniform plexus is the network of veins that drain the testicle. Plexus travels along the posterior part of the testicle with the epididymis and vas deferens, and then into the spermatic cord, which extends from the testes up through the ingiunal canal in the lower abdominal wall to the circulatory system. The vas deferens is not situated by itself but is a part of a larger tissue bundle called the spermatic cord. The spermatic cord contains many blood vessels as well as the vas deferens, nerves, and lymphatic channels. Hence care needs to be taken to avoid vas deferens and vessels to avoided permanent damage to testis.

A varicocele can develop in one or both testicles, but in most cases occurs in the left testicle. Because of the varicocele's impairment of blood flow, the blood cannot cool as it does in normal veins, and this increased temperature is thought to be a cause of infertility. The excess heat can damage sperm or impede the production of new healthy sperm.

Varices can also play a role in chronic pelvic pain syndrome in women. One of numerous causes of chronic pelvic pain in women is "pelvic congestion syndrome" (PCS), a condition in which varices form in the pelvis minor, affecting organs including the uterus, ovaries and vulva. PCS is analogous to varicoceles in men. Pelvic varices occur in around 10% of the female population, and varices occur usually in women of the ages of 20-50.

A variety of treatments have been attempted for female pelvic varices, with varying degrees of success. Medications, including vasoconstrictors and hormonal medications, have been used successfully, though they may not always provide long-term relief. Numerous surgical treatments have also been performed, including tying off or removing veins, uterine suspension, and, generally as a last resort, hysterectomy.

Numerous options are also available for treatment of male varicoceles. Surgical treatment, usually performed under general anesthetic, involves making an incision above the scrotum and tying off the veins to detour blood flow into normal veins. Such a procedure can require up to six weeks recovery time before heavy lifting can be performed, with light activities able to be performed earlier.

Embolization is a procedure used by surgeons to block fluid flow through a blood vessel or organ, and has been used to treat both male varicoceles and female pelvic varices with at least some success. An embolus, which is a mass of some material, is inserted into the blood vessel with a catheter and is lodged in the vessel to restrict blood or fluid flow. This causes a clot to develop in the vessel that closes off the vessel. Types of emboli include wire coils, sponges, "chemical cross-linking means such as cyanoacrylate", balloons, umbrella-like devices and other types of plugs. (U.S. Pat. No. 5,167,624)

U.S. Pat. No. 4,509,504 discloses the use of a device consisting of a material that swells when in contact with body fluid. The device is inserted into a body passage and the material is swelled to occlude the passage. The passages could be blood vessels (including varicose veins), urethers, spermatic ducts and oviducts. The device can purportedly be used as a contraceptive. When swelled, the device anchors in position and fully occludes the passage.

U.S. Pat. No. 6,200,332 describes a device and method for underskin laser treatment. Indications such as wrinkles and varicose veins can be treated with this invention. The handpiece uses a standard needle to insert an optical fiber under the skin or into a blood vessel, and features an extension piece that maintains the end of the optical fiber in a fixed position relative to the handpiece. The method described in this invention is generally envisioned for the treatment of tissue near the surface of the skin, for cosmetic procedures such as surface varicose veins or wrinkle removal. It is not suitable for deep interior treatments such as varicoceles or pelvic varices because of the anatomical positions and function. Again because of the anatomical position of the vein care needs to be taken to avoid damages to renal arterial, like transection, intimal tears, or thrombotic occlusion U.S. Pat. No. 5,167,624 describes a method and apparatus for passing an embolus into a blood vessel. The embolus lodges in the vessel and allows formation of a vessel-occluding clot around the embolus. The embolus is hydraulically passed through the lumen of a catheter to a given point in a blood vessel; the hydraulic fluid pushed the embolus to a predetermined position in the blood vessel. The embolus is preferably a coil that is stretched in the catheter lumen and recoils once released into the blood vessels. The recoiling causes the spring to expand and exert a force on the wall of the blood vessel to anchor it in place.

U.S. Application No. 2002/0156499 describes an apparatus and method featuring a deformable member for occluding a blood vessel. Upon application of force on the occluder, the occluder can be deformed to expand to fully occlude a vessel, and may further be anchored so that migration can be avoided.

WO 01/66016 A1 describes embolic particles, agents and compositions, visible by ultrasound, for embolization to treat various disorders such as varicocele. Microbubbles are incorporated into or around the particles to allow the particles or composition to visible by ultrasound, thus avoiding the need for fluoroscopy and contrast agents in angiography.

Embolization procedures are typically outpatient procedures that require 24 hours or less of recovery time. Disadvantages include the relative complexity of the inserted embolus and the associated delivery equipment and the increased risk of infection, migration, or other complications due to the need to deposit and secure a foreign body within the blood vessel.

Most of the procedures discussed in the prior art use invasive methods. Since varicoceles in men and pelvic varices in women are reported to involve the reproductive organs extra care needs to be taken since most patients affected are in reproductive age group. The Pampiniform plexus in the testis and pelvis minor in pelvic regions, which are affected by varices are connected to other major veins, which are again connected to other vital organs in the abdominal cavity, and are surrounded by other major arteries and nerves in the regions, hence utmost care needs to be taken while accessing this vein unlike the veins in the legs. Any damage to the other veins or artery can cause irreversible damage to reproductive organs.

In most cases the vein closure is not complete because collateral veins running parallel to testicular vein are missed, and recurrence is common. Collateral veins are difficult to identify and ligate separately from the testicular artery. Similarly access to the right internal spermatic vein is very difficult and requires significant time.

Other disadvantages include long duration of the procedure, Seduction, failure to access the internal spermatic vein, radiation exposure and recurrent varicocele. And most importantly the success of these procedures is clearly dependent upon a high level of skill and experience of the interventional radiologist.

There remains a need for a minimally invasive treatment of varicocele and other delicately placed abnormal veins that does not require the permanent or extended insertion of foreign objects and can be performed with a minimum of pain and without significant recovery time. The present invention addresses this need.

OBJECTIVES AND BRIEF SUMMARY OF THE INVENTION

It is an object of the present invention to provide an improved method for treatment of varices.

It is another object of the present invention to provide a method for treatment of varices, particularly pelvic varices, varicoceles and oesophageal varices that is minimally invasive, does not require general anesthesia, and requires little or no time for patient recovery.

It is still another object of the present invention to provide a method for treatment of pelvic varices, varicoceles, and oesophageal varices that does not require the deposition of foreign objects in the body.

Briefly stated, the present invention discloses a minimally invasive method for treating varices including pelvic varices in females, varicoceles, and also oesophageal varices. The method comprises the steps of inserting a catheter device into the blood vessels of a patient and advancing the distal end of the catheter to reach the varix or varices. The insertion may be made in the femoral vein or in other vessels as appropriate. Preferably, x-ray, angiography, or other imaging techniques are used to visualize and position the catheter. An optical fiber or optical fiber bundle is then inserted into the catheter and the distal end is advanced to a predetermined point near the varix or varices. Laser energy of preferably 980 nm is then transmitted to the varix to close the blood vessel. Imaging techniques such as angiographies may again be performed to confirm closure of the vein. The present invention is an outpatient procedure that requires no incision or general anesthesia, requires minimal recovery time, and does not require that any foreign objects be left in the body. This method has been shown to have a higher success rate than previous embolization and surgical procedures.

The above, and other objects, features and advantages of the present invention will become apparent from the following description read in conjunction with the accompanying drawings.

BRIEF DESCRIPTION OF FIGURES

FIG. 1—Illustration of the method for treatment of a varicocele.

DETAILED DESCRIPTION OF PREFERRED EMBODIMENTS

The present invention is a method for treating male and female varices located in or near the reproductive system. Due to its anatomical location within the body it is considered to be delicate when compared to leg veins and their treatment methods. Moreover the affected veins are connected to other veins which are connected to vital organs in that regions, hence this vein needs to be carefully treated to avoid irreversible damage to these organs and their function.

In particular, the method is effective for treating varicoceles in men and pelvic varices in women. It is an outpatient procedure performed under local anesthetics, can be quickly performed with a minimum of recovery time, and avoids the need to introduce foreign objects into the body, in contrast to traditional embolization treatments.

In the first step, a small catheter is inserted into the circulatory system either at the groin, preferably into the femoral vein, or through an upper access such as the subclavian vein in the arm by making a small painless incision. Preferably under X-ray imaging, the catheter is moved into position near the varicocele vein mass. Optionally, further visualization procedures such as angiographies with contrast (dye), may be performed to achieve correct positioning After the catheter is correctly positioned, a laser fiber is inserted into the catheter and secured to the catheter by a special locking system so that the distal end of the fiber extends a preselected distance from the distal part of the catheter itself. An exemplary embodiment of a locking system for use with the present invention is described in U.S. Pat. No. 6,200,332. That patent describes an underskin laser treatment device comprising a handpiece having a hollow channel and fitted with a hollow surgical needle through which an optical fiber, connected to a laser source, is inserted. The handpiece further comprises an extension that can fit into the hollow channel having a protrusion which is keyed to a groove within the channel wall for guiding the optical fiber through the handpiece and needle. This device, by virtue of the extension piece, maintains the optical fiber in a fixed position relative to, and at a fixed distance from, the handpiece, allowing the user to know how much of the fiber has been inserted into the treatment area. Laser energy having a wavelength of preferably 980 nm is then delivered following a preselected radiation protocol, which may vary by patient. Such protocol parameters include emitted power, duration of radiation or pulse, pulse length, and time between pulses.

Following irradiation, the catheter and fiber are withdrawn together until their ends reach the proximal part of the varicocele vein. The fiber is withdrawn through the catheter and dye may be injected so that further angiographies can be performed to confirm the closure of the vein. Other visualization techniques, such as echo color doppler ultrasound, may also be used.

Radiation is preferably delivered through an optical fiber or fiber bundle, and a preferred radiation source is a high power diode laser or diode array emitting at a wavelength of 980 nm. The optical fiber or bundle is connected to the radiation source at its proximal end and its distal end contains a means for distributing radiation. This radiation distribution means may take a variety of forms, including simply the bare end of the fiber or a shaped fiber tip, or including more complex means such as a diffuser. Laser energy, especially in the range of 980 nm, is effective at effecting vein closure by causing the vein wall to shrink and close off the vein. Damage to the vein wall creates a shrinking effect that acts to close off the vessel. The presence of blood in the vein plays a key role in evenly distributing thermal damage to the inner vein wall and creating damage over a wide inner surface area of the vein wall, and thus helps to more efficiently create a thrombotic occlusion and avoids simply cutting through the vein wall. Also, the radiation generates steam bubbles that serve to distribute a large amount of damaging thermal energy to large areas of the inner vessel wall. Another mechanism for closing the vein is the collapse of the vessel wall due to the 980 nm wavelength's high absorption in water. Alternatively, a large steam bubble may be generated by the radiation that forces blood from a section of the vein. This in turn makes it easier for the vessel to collapse. Additionally, the radiation can also have a coagulating effect on the blood, which can also aid in closing off or blocking the vein. These effects may act in conjunction to cause effective closure of the vein.

An advantage of the present invention is that a foreign body need not be inserted into the vein to trigger embolization. Because of this, there is no need for a mechanism to push the embolus into the vein, which simplifies both the procedure and the equipment needed. In addition, because no foreign body is left in the vein after treatment, the present invention does not introduce the risk of infection that is present in traditional embolization techniques. Also, the risk of migration, inherent in many detached occluding devices, is eliminated with the present invention.

There are numerous additional advantages of the present invention over prior art treatments. The method of the present invention does not require more than a small incision (only large enough to insert the small catheter), resulting in faster recovery and no damage to other vessels or organs and no scaring. Each of these improvements are significant to the well being of the patients. The use of general anesthetics can be avoided. Data show higher success rate then embolization. Lastly, little or no recovery time is required and patients can resume activities faster than after normal surgery.

A preferred embodiment of the present invention is illustrated in FIG. 1. In this embodiment, a varicocele above the left testicle is closed using radiation. Catheter 101 is inserted through the front of a patient's leg into right femoral vein 103. The distal end of catheter 101 is advanced through right femoral vein 103 and through left internal spermatic vein 105 to a position near varicocele 107 above left testicle 109. Next, fiber 111 is inserted into catheter 101 and advanced until distal end 113 of fiber 111 has advanced a predetermined distance from the distal end of catheter 101. A radiation source is then activated and radiation 115 closes off the veins of varicocele 107. Fiber 113 is then withdrawn and catheter 101 may be withdrawn or used in an angiography to confirm that the varicocele has been effectively closed.

The present invention is not merely limited to varicocele and female pelvic varices treatment. Oesophageal varices, which also are delicate and difficult to treat because of their placement, may also be treated successfully using the method of the present invention. Oesophageal varices are enlarged veins on the lining of the esophagus that are prone to bleeding. They are life-threatening, and can be fatal in up to 50% of patients. They usually appear in patients with severe liver disease. For treatment of this indication, the method of the present invention is similar to that described above for varicoceles and female pelvic varices. In this embodiment, the catheter is inserted into the portal vein and advanced to a point proximate to the varices. Radiation as indicated above is applied to close off the vein.

The present invention is further illustrated by the following example, where a wavelength more commonly associated with tissue ablation or cutting is successfully used, but is not limited thereby.

EXAMPLE 1 of a Varicocele Above the Left Testicle

The present invention is very effective for treating varicoceles in the spermatic cord above the testicle. In one example, in this case for a varicocele above the left testicle of a patient, a catheter is inserted into the right femoral vein and advanced so that the distal end of the catheter is approximately 1 cm from the desired site of embolization. X-ray imaging and angiography are performed to visualize this step and aid insertion.

A 400 micron optical fiber is coupled to a 980 nm diode laser, whose output lies in the range of 980±20 nm, and the fiber is advanced through the catheter until its distal end extends 1 cm from the distal end of the catheter. The fiber/catheter is fitted with a locking mechanism so that the fiber can be properly extended without further visualization or measurement.

The diode laser is activated with a power of 4-5 W, and radiation is applied in a series of pulses. Each pulse length is between 1 and 1.5 seconds long, separated by a span of 1 second between each pulse. Total irradiation time, or total time in which the laser is "on", is between 15-30 seconds, depending on the length of the vein treated.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for the treatment of varices in the genital/pelvic area or in the oesophageal area, comprising the steps of:
    a. inserting a hollow catheter having an inner lumen into a blood vessel and advancing a distal end of said catheter to a position proximate to at least one varix selected from the group consisting of a varicocele, a female pelvic varix, and an oesophageal varix;
    b. inserting an optical waveguide, whose proximal end is connected to a radiation source and whose distal end distributes radiation, into the inner lumen of said catheter;
    c. advancing said distal end of said waveguide through said distal end of said catheter to a predetermined point near said at least one varix;
    d. irradiating blood within said varix with radiation from said radiation source so as to cause closure of said at least one varix; and
    wherein said radiation has a wavelength of 980 +/−20 nm and is applied in a series of pulses, said pulses having a pulse length of about 1-1.5 second and being separated by about 1 second.

2. The method for treatment of varices according to claim 1, wherein said waveguide is selected from the group consisting of an optical fiber and an optical fiber bundle.

3. The method for treatment of varices according to claim 1, wherein said distal end of said optical waveguide comprises a bare fiber tip or a diffuser.

4. The method for treatment of varices according to claim 1, wherein said radiation source is selected from the group consisting of a diode laser and a diode laser array.

5. The method for treatment of varices according to claim 1, wherein said predetermined point is 1 cm from said distal end of said catheter.

6. The method for treatment of varices according to claim 1, comprising the additional step of utilizing x-ray and angiographic imaging to view a path of said catheter during said catheter insertion step.

7. The method for treatiiient of varices according to claim 1, comprising the additional step of utilizing echo color doppler ultrasound to view a path of said catheter during said catheter insertion step.

8. The method for treatment of varices according to claim 1, comprising the additional step of performing an additional angiography after said irradiation step to confirm closure of said varix.

9. The method for treatment of varices according to claim 2, wherein said optical fiber has a core diameter of preferably 400 microns.

* * * * *